United States Patent [19]

Close et al.

[11] Patent Number: 5,002,061

[45] Date of Patent: Mar. 26, 1991

[54] APPARATUS FOR MEASURING BLOOD PRESSURE

[75] Inventors: Alan Close; Guy Hamilton, both of Woking; Martin Wright, Rickmansworth, all of United Kingdom

[73] Assignee: Tripod Industries Company Limited, Great Britain

[21] Appl. No.: 225,557

[22] Filed: Jul. 28, 1988

Related U.S. Application Data

[63] Continuation of Ser. No. 898,239, Aug. 20, 1986, abandoned.

[30] Foreign Application Priority Data

Aug. 23, 1985 [GB] United Kingdom ............... 8521207
Sep. 20, 1985 [GB] United Kingdom ............... 8523335

[51] Int. Cl.$^5$ .................................................. A61B 5/02
[52] U.S. Cl. .................................... 128/677; 128/687; 128/722
[58] Field of Search ................. 128/672, 677–690, 128/722, 774, 782

[56] References Cited

U.S. PATENT DOCUMENTS

| | | | |
|---|---|---|---|
| 2,755,796 | 7/1956 | Boucke | 128/687 |
| 3,056,401 | 10/1962 | Greenspan | 128/681 |
| 3,104,661 | 9/1963 | Halpern | 128/683 |
| 3,156,235 | 11/1964 | Jaeger | 128/689 |
| 4,292,850 | 10/1981 | Bachem | 73/718 X |
| 4,295,471 | 10/1981 | Kaspari | 128/687 X |
| 4,324,259 | 4/1982 | Wright | 128/722 |
| 4,326,537 | 4/1982 | Croslin | 128/687 |
| 4,337,778 | 7/1982 | Akira et al. | 128/680 |
| 4,381,788 | 5/1983 | Douglas | 128/722 |
| 4,459,991 | 7/1984 | Hatschek | 128/682 X |
| 4,464,123 | 8/1984 | Glover et al. | 128/681 X |
| 4,469,099 | 9/1984 | McEwen | 128/682 X |
| 4,561,447 | 12/1985 | Kawamura et al. | 128/687 |
| 4,581,676 | 4/1986 | Baxter et al. | 73/718 X |
| 4,606,228 | 8/1986 | Whitmore | 73/718 |

FOREIGN PATENT DOCUMENTS

| | | | |
|---|---|---|---|
| 1466899 | 2/1969 | Fed. Rep. of Germany | 128/677 |
| 1466900 | 5/1969 | Fed. Rep. of Germany | 128/677 |

Primary Examiner—Max Hindenburg
Assistant Examiner—John P. Lacyk
Attorney, Agent, or Firm—Ostrolenk, Faber, Gerb & Soffen

[57] ABSTRACT

The invention relates to apparatus for measuring blood pressure by providing an inflatable cuff and pulse sensing means for fixing to a digit such as, for example, a finger or toe, and electrical control circuit means for converting a sense pulsed into a visual or audible indication, pneumatic means for transmitting the sensed pulse to the converting means and pressure means for measuring the pressure exerted in the cuff, the arrangement being such that with the cuff in a operative position on the body, progressive inflation/deflation of the cuff is effected until pulse sensing means just detect the presence of the pulse thus providing an indication of the systolic blood pressure. The invention includes novel variable capacitors for pneumatic coupling to the pulse sensor and comprising a housing, a diaphragm disposed across the housing, a base plate disposed on the side of the diaphragm opposite from said pneumatic connection, and electrical connecting means provided to the base plate so that changes in the volume occur the cavity defined by the base plate and the diaphragm due to pressure changes in the pneumatic system above the diaphragm, resulting in changes in capacitance and sensing of the pulse within the pneumatic system to be determined.

28 Claims, 6 Drawing Sheets

APPARATUS FOR MEASURING BLOOD PRESSURE

This is a continuation of Application Ser. No. 898,239 filed on Aug. 20, 1986 now abandoned.

BACKGROUND OF THE INVENTION

The present invention relates to apparatus for measuring blood pressure.

Hitherto, blood pressure has been measured by providing an inflatable cuff which is wrapped around the upper arm, and inflated. The pressure within the cuff is monitored by means of a mercury manometer.

In use, the device is wrapped around the upper arm of a patient and a pulse is detected using a stethoscope usually from the artery in the elbow. The cuff is inflated until the pulse is no longer audible and then the pressure is slowly released and the pressure at which the pulse just becomes discernable is noted. This is known as the systolic blood pressure. The pressure is further released progressively until the audibility of the pulse changes and the effect of the pulse becomes more muffled. The pressure at which this occurs is known as the diastolic blood pressure.

In order to determine a person's blood pressure, it has always been thought necessary to take both the systolic and the diastolic pressures. Recent research, however, has indicated that probably the more important pressure measurement is the systolic pressure, that is to say, the highest pressure to which blood is subjected.

Furthermore, existing methods of taking blood pressure usually require a patient, at least to a limited extent, to undress to reveal the upper arm and secondly, requires a second person to manipulate a stethoscope in order to detect the pulse and changes in pulse necessary to record the pressures concerned.

Accordingly, there is a major need for a method of measuring blood pressure which does not require the patient to undress and which can be self-administered.

Summary of the Invention

According to the present invention, there is provided apparatus for measuring blood pressure which apparatus comprises:
- an inflatable cuff for affixing to a body in a position to obturate an artery,
- inflation means for progressively inflating/deflating said cuff, and
- pulse sensing means for sensing a pulse, characterised by
- means for converting the sensed pulse into a visual indicator,
- pneumatic means connecting said pulse sensing means and said converting means,
- and pressure means for measuring the pressure exerted in said cuff, whereby with the cuff in operative position on a body and the pulse sensing means in pulse sensing contact with said body at a point of said cuff, progressive inflation/deflation of said cuff is effected until the pulse sensing means just detects the presence of a pulse thus providing an indication of the systolic blood pressure by said pressure measuring means.

In one embodiment of the invention, the cuff is adapted to encircle a digit, such as a finger, thumb or toe; the inflation means may be a piston acting within a cylinder connected with said pressure measuring means and actuated to inflate the cuff. The pulse sensing means which may be a spherometer of the type as claimed in any one of the claims of patent specification No. 1,604,251, which is contacted with the digit downstream of the cuff to sense the presence or absence of a pulse. The piston is screw threaded with respect to the cylinder for progressive control of the piston within the cylinder.

The electrical means may include means for detecting changes in capacitance of the variable capacitor forming the subject of U.S. Pat. No. 1,604,251 and may further include means for generating a voltage in response to said changes in capacitance. The visual indication of pulse may be given by a light emitting diode excited by the voltage so generated.

In a further embodiment of the present invention, the barometeric means may be an aneroid barometer. Any electrical means may be powered by batteries and a micro switch may be included within the pneumatic system for the inflation/deflation of the cuff so that the electrical current supply to the electrical means is operative only when the pressure within said pneumatic system rises above a predetermined datum.

The present invention also includes a variable capacitor comprising:
- a housing having a pneumatic connection thereto,
- a conducting diaphragm disposed across said housing,
- a base plate disposed on the side of the diaphragm opposite said pneumatic connection and electrical connecting means provided to the base plate and the diaphragm, whereby in a datum position the diaphragm is maintained in spaced relationship from said base plate to provide a datum capacitance and changes in the pressure via the pneumatic connection cause flexing of the diaphragm thereby varying the spacing therebetween with the base plate, thus producing an alternation in the capacitance between the connectors for the diaphragm and the base plate.

In essence, therefore, the conducting diaphragm is stretched over a cavity having in its base a metal electrode thereby forming a condenser with an air dielectric whose capacity can be varied by varying the volume under the diaphragm.

The diaphragm is preferably a metallised plastics diaphragm typically of a polyethylene terephthalate film, commercially available under the trade names Melinex or Mylar; such a film of thickness 0.010 to 0.014 mm metallised on one side with aluminium or tin has been found to be suitable.

Means may also be provided for separate insulation of the diaphragm from the base plate. In a preferred embodiment the base plate is provided with a central raised portion and a raised annular rim; the diaphragm may be stretched over said rim for clamping between the rim and the body in assembly of the device.

The factors controlling the performance of the capacitor are as follows:

Capacity varies as $D^2/h$ where $D$ is the diameter of the fixed electrode and $h$ is the thickness of the dielectric.

The deflection of the diaphragm for a given pneumatic pulse varies inversely as the square of its diameter, provided that it is so thin and lightly stretched that the pressure required to deflect it is negligible with the size of pulse which the device is designed to detect.

If the circuit used measures per cent and not absolute change of capacity the system is insensitive to electrode diameter or air-gap and, provided the changes are small (less than 2%), the response is practically linear. The overall sensitivity varies as the applied voltage, which must therefore be stabilised for critical applications. Within limits, the sensitivity is increased by decreasing diaphragm diameter, the limits being that the absolute capacity must not be so small as to present difficulties with connections, and the stiffness of the diaphragm must not become significantly increased.

In a further embodiment the rim projects by an amount of the order of 0.01 to 0.005 mm preferably 0.025 mm–0.05 mm from the surface of the central portion of the base plate so that in its datum position the diaphragm has a spacing therefrom within a similar range.

The housing portion may be made of a flexible molded plastics material such as a polyamide, polypropylene, or acetyl resin.

A device in accordance with the present invention is easy to produce and easy to assemble and gives constant diaphragm tension. The size can be set to requirements, for example, 15 mm diameter gives about 7 and the sensitivity is sufficient to detect extremely small pulses in a pneumatic system. The device may be mounted on a board or fitted with a lever socket for direct connection to the pneumatic system.

Following is a description by way of example only and with reference to the accompanying drawings of methods of carrying the invention into effect.

DETAILED DESCRIPTION OF THE PREFERRED EMBODIMENTS

Figure 1:
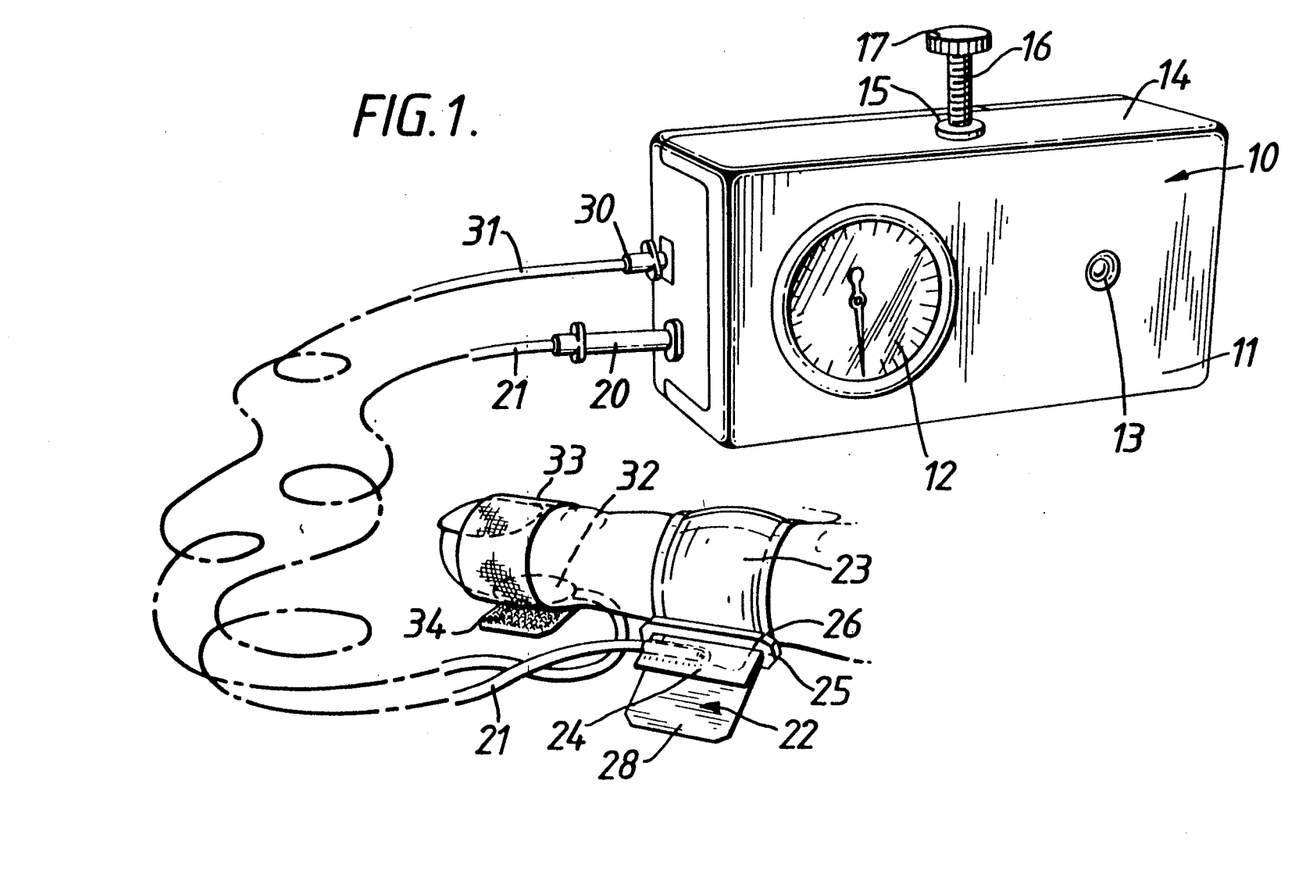
FIG. 1 is a perspective view of a device in accordance with the present invention.
Figure 2:
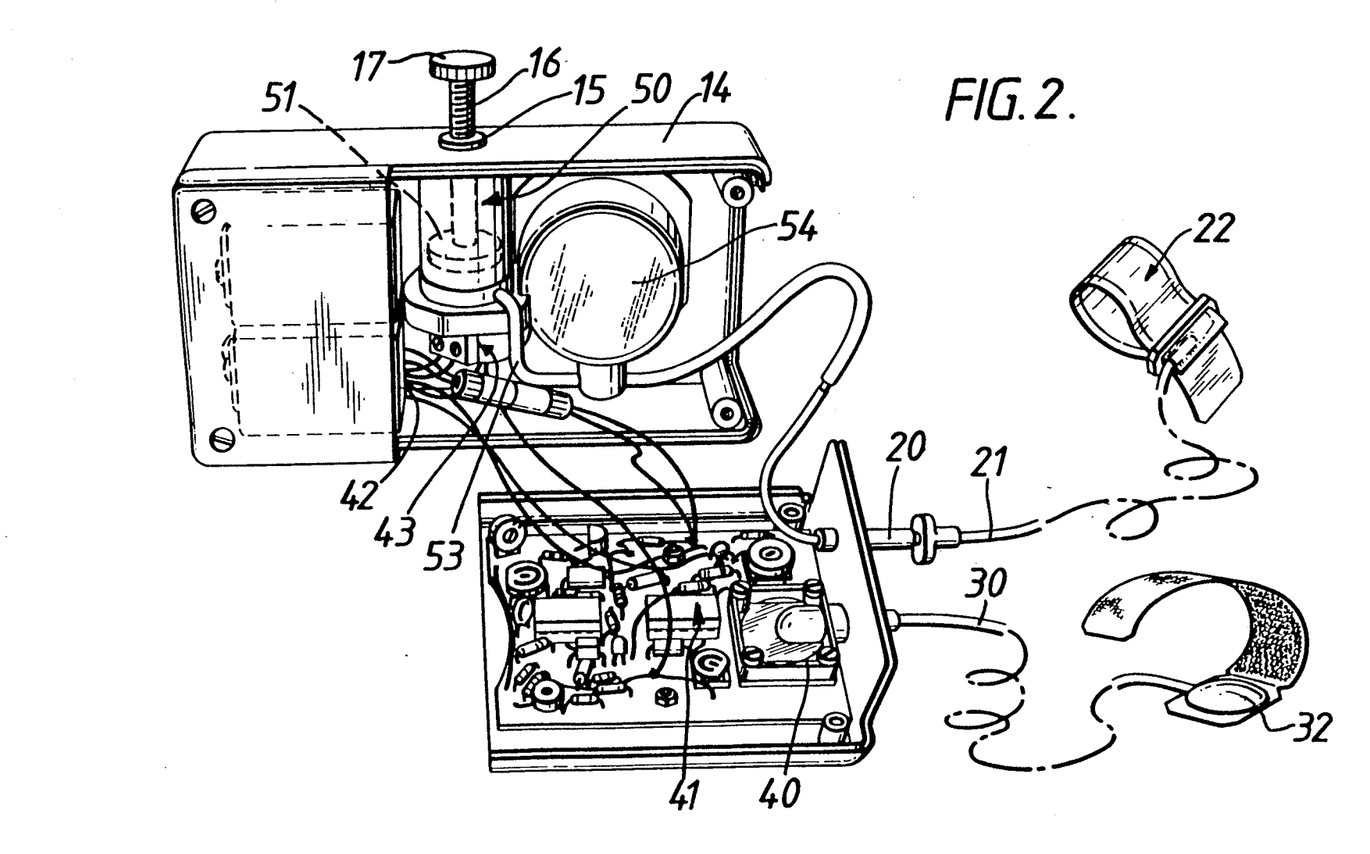
FIG. 2 is a back view of the device of FIG. 1 in a disassembled condition.

Turning first to the apparatus illustrated in FIGS. 1 and 2 of the accompanying drawings, a housing indicated generally at 10 having a front face 11 thereof, carries an aneroid barometer 12 and a light emitting diode 13. An upper side face 14 of the housing 10 is provided substantially centrally thereof, with a threaded bore 15 which accommodates a threaded plunger 16 having a knurled knob 17 at an outer extremity thereof.

An end face is provided with a pair of pneumatic connections 20 and 30. Pneumatic connection 20 is coupled, by means of a air conduit 21, to an inflatable cuff indicated generally at 22 comprising a strip like bag 23 of plastic having a connection for conduit 21 at one end 24 thereof and a constraining clip 25 comprising a planar piece of plastic having a longitudinal slot 26 therein adapted to accommodate two thicknesses of cuff 22. In use the cuff is wrapped around a finger and the end 28 remote from connection 24 is tucked into the slot 26 in clip 25 in juxtaposition with end 24 and pulled tight, the arrangement being such that inflation of cuff via conduit 21 will result in expansion of bag 23 and produce a constriction of an artery 24 located in the finger to which the cuff is applied.

Pneumatic connection 30 is provided by means of a conduit 31 to an abdominal spherometer 32 as described and claimed in British patent specification No. 1,604,251. This spherometer is secured to a tape 33 adapted to encircle a finger tip with the spherometer in contact with the skin. The tape is provided with releasable fastening means 34 such, for example, as "velcro". The purpose of the spherometer is to detect the existance of a pulse in the fingertip by sensing pneumatically the pulse and transmitting the resulting pneumatic pulses via conduit 31 to a transducer responsive to variations in the volume of a capsule due to expansion and contraction in response to the pulse sensed at the end of the finger.

Turning now to FIG. 2, it will be seen that the spherometer 32 is connected to a variable capacitor 40 having a fixed electrode and a movable electrode as hereinafter described. A detector circuit indicated generally at 41 serves to detect variations in the capacitor 40 and to convert the variations in capacitor 40 into variations in voltage so that each variation in the capacitor 40 results in a corresponding flash of LED 13. The electrical conversion circuit indicated generally at 41 is powered by means of batteries 42 which are connected to the circuit by means of a microswitch indicated generally at 43.

The microswitch 43 is carried at the base of a cylinder 50 having a piston 51 therein which is carried at the extremity of a threaded plunger 16, the arrangement being such that rotation of knurled knob 17 results in insertion/withdrawal of the plunger and corresponding movement of piston 51 to expel air from or withdraw air into the cylinder 50 by means of conduit 53 and connection 20 and 21 to cuff 22. Conduit 53 is connected with an aneroid barometer 54, the face of which 12 is exposed on forward front face 11 of housing 10.

In its datum position the knurled knob 17 is unscrewed to withdraw plunger 51 to the upper end of cylinder 50. The spherometer 52 is then applied in its operative position as shown in FIG. 1 to a fingertip and the cuff 22 is inserted around the face of the finger, the free end 28 being secured using the clip 25 in the manner shown.

In operation, the knob 17 is then screwed progressively inwards to drive air from the cylinder via conduits 53, 20 and 21 into cuff 22, thus inflating cuff 22 and exerting pressure on the artery within the base of the finger, serving to squeeze the artery against the bone therein. When the pressure exerted by the piston 51 has reaced a predetermined level, microswitch 43 triggers to connect batteries 42 to electrical means 41. The spherometer 32, sensing a pulse in the fingertip, produces changes in capacitance of chamber 40; this capacitance change is detected by electrical means 41 to produce corresponding flashing of LED 13 in time with the pulse. The knurled knob 17 is screwed in to further depress plunger within cylinder 50 and express more air into cuff 22 thus increasing the air pressure therein which is measured by means of aneroid baramater 54.

This is continued until the LED 13 ceases to flash which means that the spherometer 32 has ceased to detect the presence of a pulse in a fingertip. The piston 51 is then withdrawn slightly by uncrewing knurled knob 17 until the LED 13 just begins to flash. At this point the pressure indicated by the aneroid barometer 54 corresponds to the systolic blood pressure.

On completion of the measurement, the knurled knob 17 is unscrewed completely to withdraw plunger 51, thus deflating cuff 22 and at the same time lowering the pressure within the cuff pneumatic system to below the threshold at which microswitch 43 triggers. Microswitch 43 thus switches to the "Off" position thus isolating the batteries and terminating flashing of LED 13.

The embodiment illustrated in FIGS. 3 to 6 of the accompanying drawings operates on the same principal as described above. In this case, however, the housing is provided towards one end with a hinged flap 60 which reveals a liquid crystal display 61, a pump 62 and a pressure release control 63.

Figure 5:
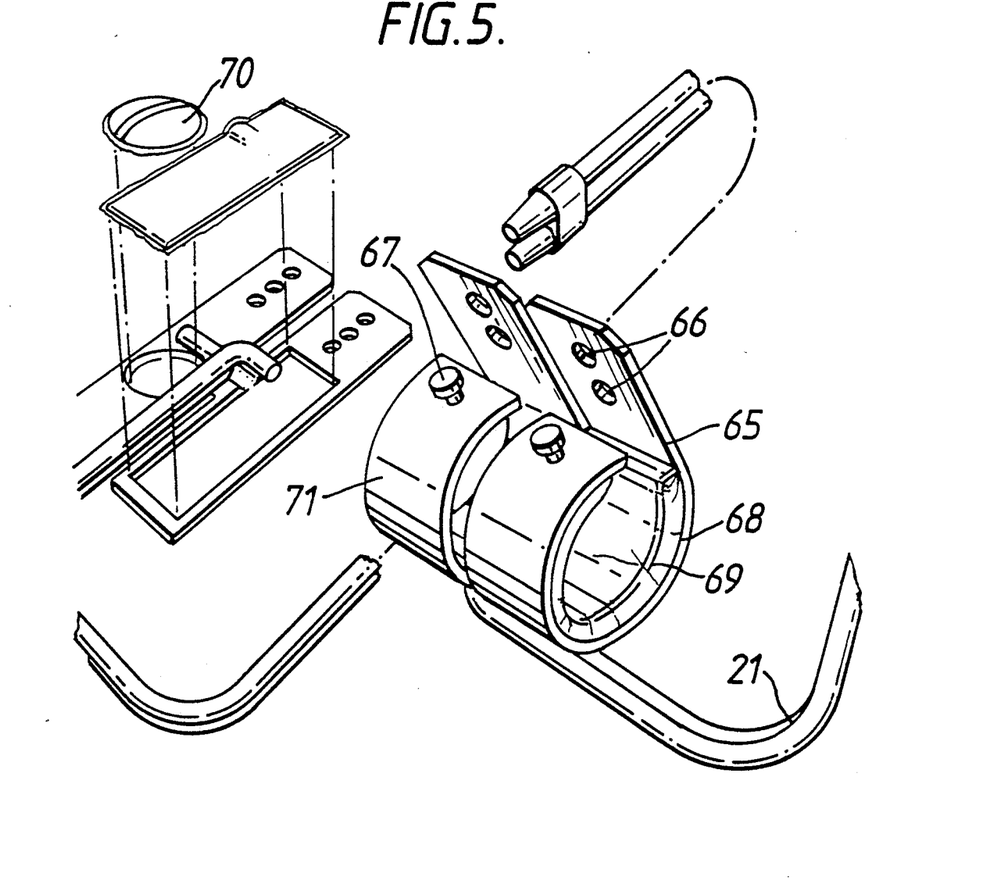
FIG. 5 is a detail of the cuff for use with the apparatus of FIG. 3.

The cuff assembly is illustrated in FIG. 5 and comprises a pair of shaped digit encircling elements 65, 71 and having, in this embodiment, a pair of longitudinally spaced holes 66, each of which hole 66 is adapted to engage with a stud 67 for securing each strap 65, 71 about a digit. Strap 65 carries on its internal surface 68 an inflatable cuff portion 69 which is connected via an orifice in strap 65 to pneumatic line 21 for connection to a pieso-resistive pressure transducer located within housing 10, while strap 71 carries a spherometer 70 also connected by means of a pneumatic line to a variable capacitor within housing 10.

In operation of the device, the straps 65 and 71 encircle a digit so that a fingertip rests on a spherometer 70 housed in strap 71 with the cuff 69 encircling the digit upstream (as far as the blood flow is concerned of the fingertip or area being sensed by the spherometer 70). The straps are fastened by engaging the appropriate holes 66 with corresponding studs 67 on each of the straps.

Figure 3:
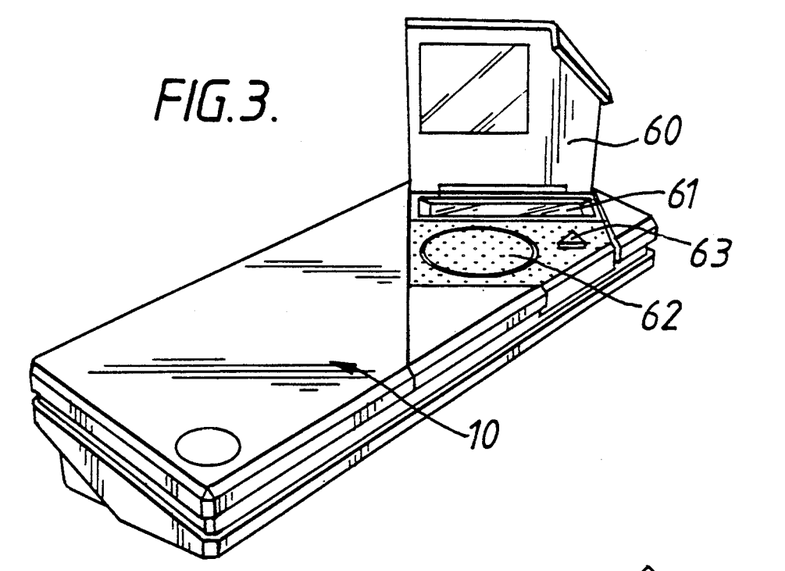
FIG. 3 is a perspective of another embodiment of the present invention.
Figure 4:
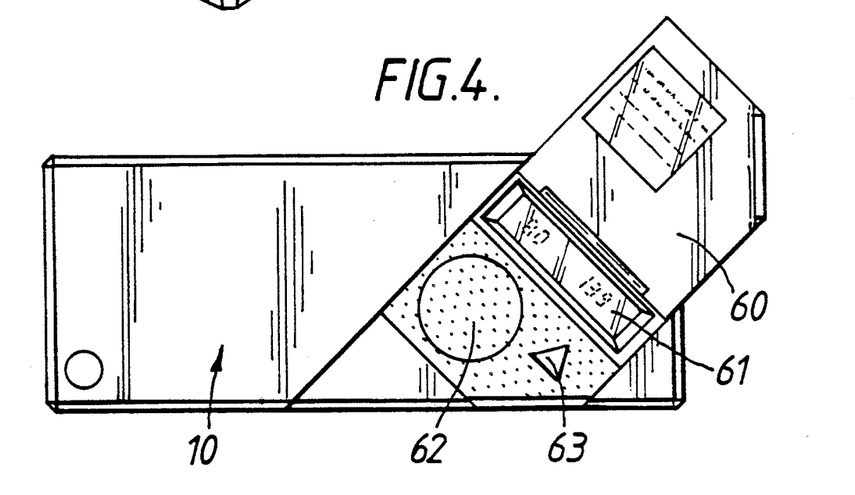
FIGS. 4 and 4a are a plan view and detail respectively of FIG. 3.
Figure 4A:
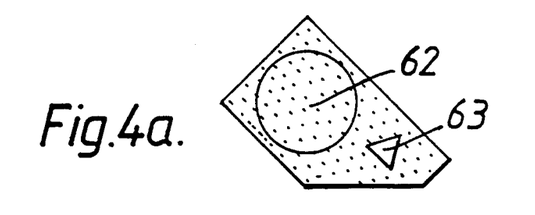

The electronics to the electrical control circuit of the device is then rendered operative by depression of the pump 63 activating the electrical system to produce a readout of a pulse in liquid crystal display 61 as sensed by the spherometer 70 while further operation of the pump blister 62 will cause inflation of the cuff 69. The pulse is sensed by the liquid crystal display 61 and the sounding of a buzzer at each time a pulse is detected. Inflation of the cuff 69 by the operation of pump 62 continues until a pulse is no longer detected. Pressure is released by depression of button 63 until a pulse is just detected by the spherometer 70 at which case deflation of the cuff is terminated and the pressure recorded by the pressure means and displayed in the liquid crystal is taken as the systolic blood pressure.

Figure 6:
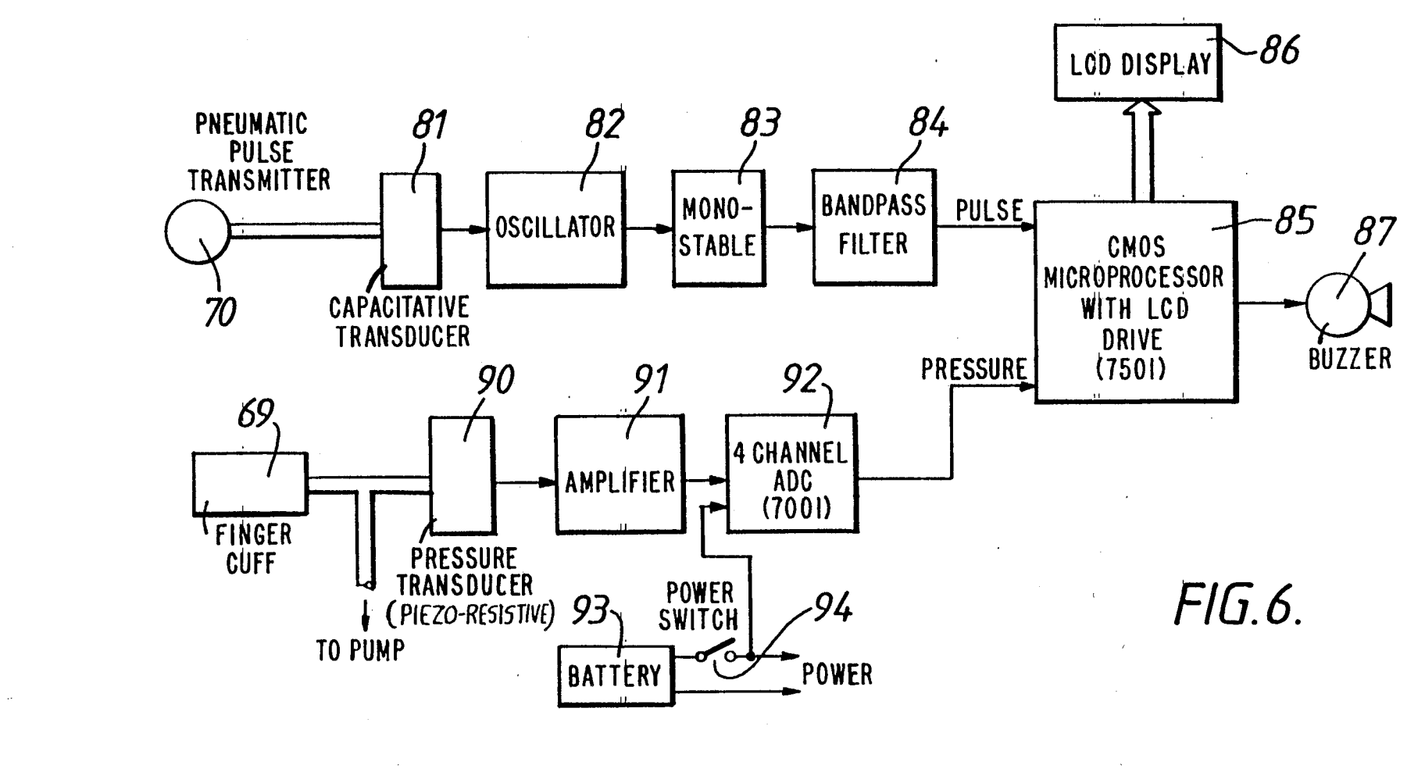
FIG. 6 is a block diagram of the circuit of the apparatus of FIG. 3.

The block diagram of the control circuit is shown in FIG. 6. The spherometer 70 is connected via a pneumatic line to variable capacitor 81 and the output signals are then passed through an oscillator 82, a monostable 83 to bandpass filter 84 and thence as a pulse to a CMOS microprocessor with LCD drive whereby the incoming pulses are compared against a time base and displayed as pulses per minute on LCD display 86. At the same time each pulse is detected by buzzer 87.

The pressure in the finger cuff 69 is detected by means of a piezo-resistive pressure transducer 90 the signal from which is passed via amplifier 91 and to a four channel ADC unit 92 which then provides a measure of pressure for display in LCD display 86. The unit is powered by means of battery 93 via power switch or pressure operated microswitch 94 operating in the manner as described with reference to FIGS. 1 and 2.

Figure 7:
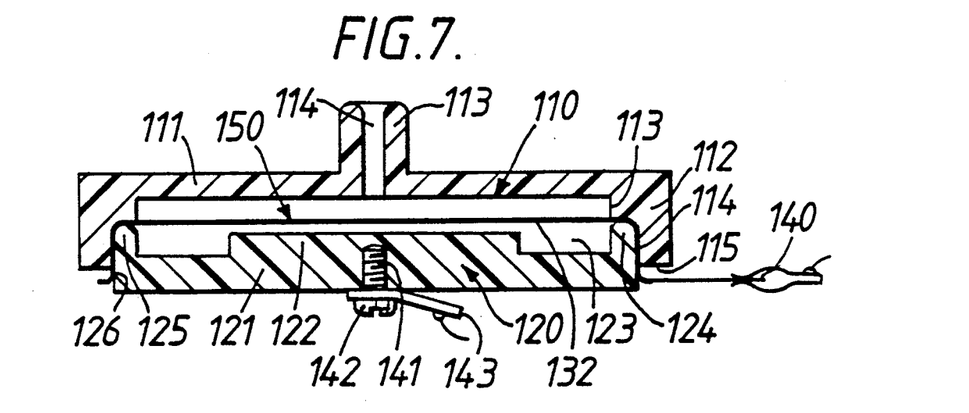
FIG. 7 is a section through a pneumatic variable capacitor for use in the apparatus of the invention.

The variable capacitor for use in the apparatus to convert pulses sensed by the spherometer 70, or 33 to electrical signals comprises a housing 110 having a circular upper wall 111 and a depending cylindrical side wall 112. The circular upper wall 111 is provided with a central cylindrical boss 113 having a through bore 114 which passes through a corresponding opening in disc 111 substantially coaxial therewith and which constitutes a connection for a pneumatic system (not shown). The wall 112 is provided on its inner surface 113 with an annular rebate 114a and terminates at its lower end in a lower annular edge 115.

The lower base plate 120 comprises a disc portion 121 which is provided with a central upstanding portion 122 to define an annular well 123 in an upper surface thereof. The periphery of annular well 123 is defined by means of an upstanding rim 124, the rim edges 125 of which are radiused. The radial dimensions of the disc 121 as defined by the external cylindrical wall 126 is arranged to be an interference fit with the internal surface 114 of the rebate in cylindrical wall 112 of housing 110. A metallised plastic diaphragm 132 comprising polyethylene teraphthalate film having a layer of metal such as aluminium or tin on a side thereof towards opening 114 is disposed across the edges of rim 124 which is then inserted into the open end of cylindrical wall 112 so that the side walls 126 thereof are an interference fit therewith. Thus the inner cylindrical wall 114 of the rebate in the lower portion of wall 112 and serve at the same time to clamp and tension diaphragm 132 in position.

The diaphragm 132 is provided with a connector 140 and the base plate 122 incorporates on the surface of the raised portion a disc electrode which may be of metal or may be a metal coated disc of small thickness electrically connected with screw 142 and connection tag 143.

In operation the terminals 140 and 143 are connected with an electrical circuit thus providing a capacitance between the metallised layer on the upper side of diaphragm 132 as shown in the diagram and the surface of the raised portion 122 of base plate 120.

Connection of the boss 113 and opening 114 to a pneumatic system enables changes in pressure in said system to be sensed by the diaphragm chamber 150 defined by the housing 111 and the diaphragm 132. Changes in pressure in said chamber 150 will result in flexing of the diaphragm 132 thus producing a change in the spacing between diaphragm 132 on the one hand and the upper surface of raised portion 122 on the other. This change will result in a change in capacitance of the device which can then be measured by the appropriate electric circuit.

In the embodiments shown in FIG. 7 the extremity of the rim edge 125 is spaced 0.002 mm above the plane of the surface of raised portion 122 of base plate 120. In its datum position, therefore, this provides for a spacing between the diaphragm and the raised portion of the base plate of 0.002 mm.

The two part housing 110 is preferably made of a flexible plastics material, such as a polyamide available under the trade name "Nylon", polypropylene, acetyl resin or any other plastics material having similar properties.

Figure 8:
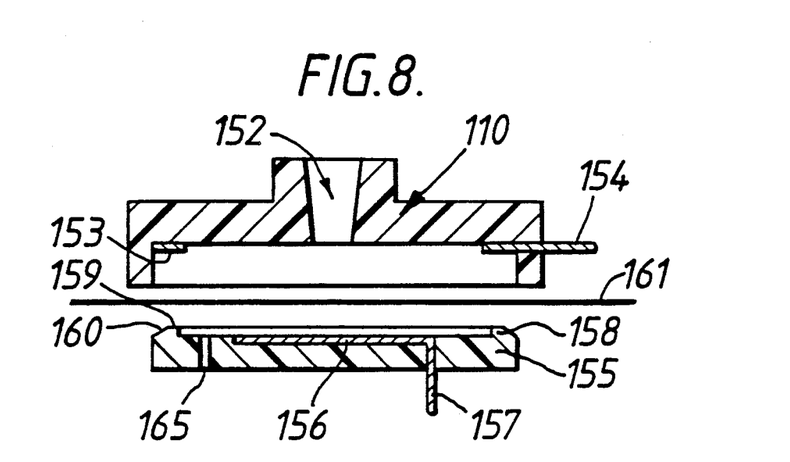
FIG. 8 is a section through an alternative embodiment of variable capacitor.

Turning now to the embodiment illustrated in FIG. 8 of the accompanying drawings, the body 110 has a Luer socket 152 for insertion of the pneumatic line from the spherometer 70, or 33. A metal connecting ring 153 with a metal soldering tag 154 is moulded integrally with the upper part of housing 110. The base plate 155 is made of the same material and has a circular metal electrode 156 moulded in a recess thereof in the upper surface thereof with a connecting tag 157 depending from the underside of base plate 155. The electrode 156 is a disc located centrally of the base plate. The base plate has an annular rim 158 having an upper annular face 159 and a sloping outer surface 160, the arrangement being such that the annular face 159 projects 0.025 to 0.050 mm above the upper surface of electrode 156 as shown in FIG. 8.

The diaphragm 161 is formed of a polyethylene teraphthalate film of thickness 0.012 mm and metallised on the upper surface. The capacitor is assembled by placing the diaphragm on the base plate with the metallised surface upwards and pressing the body on to it. The close fit between the rim 158 and the depending annular wall of housing 110 engages the edges of the film 161 to produce an interference fit between three components. Pressing the base plate home into upper housing portion results in a metallised layer on the Mylar film 161 being pressed into intimate contact with the annular electrode 156 carried by the upper housing portion and at the same time, tensions the Mylar film by means of the relative friction during the interference fit between the rim 158 and the cooperting depending wall of the upper housing portion. A sealing compound may be incorporated around the inner surface of the depending walls of the upper housing part in order to ensure a complete seal between the film 161 and the housing.

Where AC coupling is to be employed, a small leak is necessary and this is provided by making the tag on the contact ring a slightly loose fit in the molding. For DC recording the space above the diaphragm must be airtight but the space below must be vented through a small hole 165 provided in the base plate.

The diameter of the lower electrode should be of the order of two thirds of that of the diameter of the rim 158 because the peripheral part of the diaphragm moves so little that it produces an effectively fixed shunting capacity which reduces the percentage change. It will be appreciated by the man skilled in the art that the main factor governing the sensitivity of the device is the tension of the diaphragm and this can be maintained to within two or three percent a datum during production provided the two parts are moulded together in the same mould.

The device described and illustrated above provides a facile means for detecting a pulse and measuring systolic blood pressure. In the device of FIGS. 1 and 2 it will be appreciated that the flashing of the LED 13 can be coupled to a timebase to register a pulse rate and that the operation of the plunger 16 could be effected by means of a servomechanism coupled to the output from the varible capacitor 40 thus providing a fully automated means of recording systolic pressure. The device described above has the particular advantage that it is small, compact, simple to use and robust. It can be operated directly by the patient and does not require skilled nursing care and the ability to use a stethoscope in order to obtain accurate readings as systolic blood pressure.

We claim:

1. Apparatus for measuring blood pressure, comprising:
    an inflatable cuff for affixing to a body in a position to obturate an artery;
    manually operable inflation means, connected to the inflatable cuff, for progressively inflating/deflating said cuff;
    pressure means coupled and responsive to the pressure in the inflatable cuff for measuring the pressure exerted in said cuff;
    pulse sensing means for sensing a pulse of the body;
    converting means, coupled to the pulse sensing means, for converting the pulse into an indication which is perceivable visually/audibly and means for coupling the pulse sensing means to the converting means; and
    a pressure sensitive microswitch coupled to the pressure developed by the inflation means and effective to connect an electrical current supply to the converting means only after the pressure rises above a predetermined value.

2. An apparatus as claimed in claim 1, including pneumatic means, coupled between said pulse sensing means and said converting means, for pneumatically coupling said pulse sensing means to said converting means.

3. Apparatus as claimed in claim 2 wherein the cuff is configured to encircle a digit of the body.

4. Apparatus as claimed in claim 2 wherein the inflation means comprises a cylinder and a piston and the piston acts within the cylinder and is coupled to said pressure measuring means and said cuff.

5. Apparatus as claimed in claim 4 including a screw and wherein the piston is controlled by the screw to provide progressive control of the piston within said cylinder.

6. Apparatus as claimed in claim 2 wherein the pressure measuring means comprises an aneroid barometer or a pressure transducer.

7. Apparatus as claimed in claim 2 wherein the pulse sensing means comprises a spherometer.

8. Apparatus as claimed in claim 2 wherein the converting means includes means for converting pneumatic pressure pulses to electrical signals at a position remote from said cuff.

9. Apparatus as claimed in claim 2 wherein the converting means includes a variable capacitor, means for detecting changes in capacitance therein and means for generating a signal in response thereto.

10. Apparatus as claimed in claim 2 wherein the converting means includes microprocessor means and an L.C.D. drive for converting input signals to display pressure and pulse rate.

11. Apparatus as claimed in claim 2 wherein the converting means includes indicating means for indicating the presence of a pulse by an L.E.D. or by a liquid crystal display.

12. An apparatus as claimed in claim 2 wherein said inflation means, said pressure means, said converting means, said pneumatic means, and said pressure sensitive microswitch are all located together in a self contained housing and wherein said inflatable cuff is coupled to said housing solely by a single first pneumatic conduit and wherein said pulse sensing means is coupled to said housing solely by a single second pneumatic conduit.

13. An apparatus as claimed in claim 12 wherein said inflatable cuff includes means for adjusting the cuff to fit variously sized digits.

14. An apparatus as claimed in claim 12 wherein said pulse sensor means includes means for adjusting said pulse sensor means to fit variously sized digits.

15. An apparatus as claimed in claim 2 in which said pneumatic and converting means include:
    a housing having a pneumatic connection thereto;
    an unperforated diaphragm disposed across said housing;
    a base plate disposed on a side of said diaphragm located oppositely to said pneumatic connection; and
    electrical connecting means for providing a first electrical connection to said base plate and a second electrical connection to said diaphragm.

16. An apparatus for measuring blood pressure, comprising:
    an inflatable cuff for affixing to a body in a position to obturate an artery;
    manually operable inflation means connected to the inflatable cuff for progressively inflating/deflating said cuff;
    pressure means, coupled to the inflatable cuff, for measuring the pressure exerted in said cuff;
    pulse sensing means for sensing a pulse of the body;
    converting means for converting the pulse into a visual/audible indication;
    pneumatic means for pneumatically coupling said pulse sensing means to said converting means; and
    said converting means including a variable capacitor having:
    a housing having a pneumatic connection thereto;
    an unperforated diaphragm disposed across said housing and having one side disposed to said pneumatic connection;
    a base plate disposed on a side of the diaphragm located opposite said pneumatic connection;
    electrical connecting means for providing a first electrical connection to the base plate and a second electrical connection to the diaphragm;
    whereby in a datum position the diaphragm is maintained in spaced relationship from said base plate to provide a datum capacitance and changes in the pressure via the pneumatic connection cause flexing of the diaphragm thereby varying the spacing between the base plate and the diaphragm, thus producing an alteration in the capacitance between the first and second electrical connections; and
    a pressure sensitive microswitch which is coupled to the pressure developed by the inflation means and which is effective to connect an electrical current supply to the converting means but only when the pressure rises above a predetermined value.

17. An apparatus as claimed in claim 16 wherein said diaphragm is a metallized plastic diaphragm.

18. An apparatus as claimed in claim 17 wherein said diaphragm is metallized with tin or aluminum.

19. An apparatus as claimed in claim 16 wherein the housing is formed of a molded plastic material.

20. An apparatus as claimed in claim 16 wherein the base plate has an opening to the atmosphere.

21. An apparatus as claimed in claim 16 wherein the housing and the base plate are configured such that they are a press fit one to the other with the diaphragm being so disposed between the housing and the base plate that pressing the base plate and the housing together tensions the diaphragm.

22. Apparatus for measuring blood pressure, comprising:
    an inflatable cuff for affixing to a body in a position to obturate an artery;
    inflation means, connected to the inflatable cuff, for progressively inflating/deflating said cuff;
    pressure means coupled and responsive to the pressure in the inflatable cuff for measuring the pressure exerted in said cuff;
    pulse sensing means for sensing a pulse of the body;
    converting means, coupled to the pulse sensing means, for converting the pulse into an indication which is perceivable visually/audibly and means for coupling the converting means and the pulse sensing means to one another; and
    a pressure sensitive microswitch coupled to the pressure developed by the inflation means and effective to connect an electrical current supply to the converting means only after the pressure rises above a predetermined value.

23. A variable capacitor comprising:
    a housing having a pneumatic connection thereto;
    an unperforated diaphragm disposed across said housing and having one side disposed to said pneumatic connection;
    a base plate disposed on and spaced from a side of the diaphragm located opposite said pneumatic connection;
    electrical connecting means for providing a first electrical connection to the base plate and a second electrical connection to the diaphragm; and
    whereby in a datum position the diaphragm is maintained in spaced relationship from said base plate to provide a datum capacitance and changes in the pressure via the pneumatic connection cause flexing of the diaphragm thereby varying the spacing between the base plate and the diaphragm, thus producing an alteration in the capacitance between the first and second electrical connections.

24. A capacitor as claimed in claim 23 wherein the diaphragm is a metallized plastic diaphragm.

25. A capacitor as claimed in claim 24 wherein the diaphragm is metallized with tin or aluminum.

26. A capacitor as claimed in claim 23 wherein the housing is formed of a molded plastic material.

27. A capacitor as claimed in claim 23 wherein the base plate has an opening to the atmosphere.

28. A capacitor as claimed in claim 23 wherein the housing and base plate are configured such that they are a press fit one to the other with the diaphragm disposed therebetween so that on pressing the components together, the diaphragm is suitably tensioned for use.

* * * * *